United States Patent [19]

Scheler et al.

[11] Patent Number: 5,114,816

[45] Date of Patent: May 19, 1992

[54] RADIATION-SENSITIVE COMPOUNDS, RADIATION-SENSITIVE MIXTURE PREPARED THEREWITH AND COPYING MATERIAL

[75] Inventors: Siegfried Scheler, Wiesbaden; Gerhard Buhr, Koenigstein; Helmut Lenz, Hattersheim; Klaus Bergmann, Mainz-Bretzenheim; Herbert Siegel, Hofheim/Taunus, all of Fed. Rep. of Germany

[73] Assignee: Hoechst Aktiengesellschaft, Frankfurt am Main, Fed. Rep. of Germany

[21] Appl. No.: 431,221

[22] Filed: Nov. 3, 1989

[30] Foreign Application Priority Data

Nov. 4, 1988 [DE] Fed. Rep. of Germany ........ 3837500

[51] Int. Cl.$^5$ .................... G03F 7/023; G03F 7/039
[52] U.S. Cl. .................... 430/192; 430/165; 430/193; 534/556; 534/557
[58] Field of Search .................... 430/165, 193, 192; 534/556, 557

[56] References Cited

U.S. PATENT DOCUMENTS

| | | | |
|---|---|---|---|
| 737,967 | 9/1903 | Schmidt | 534/557 |
| 2,797,213 | 6/1957 | Moore | 260/141 |
| 3,046,118 | 7/1962 | Schmidt | 96/33 |
| 3,046,119 | 7/1962 | Sus | 430/193 |
| 3,046,122 | 7/1962 | Sus | 430/193 |
| 3,264,104 | 8/1966 | Reichel | 96/33 |
| 3,869,292 | 3/1975 | Peters | 96/115 R |
| 3,984,250 | 10/1976 | Holstead et al. | 534/557 |
| 4,104,070 | 8/1978 | Moritz et al. | 96/36 |
| 4,397,937 | 8/1983 | Clecak et al. | 430/192 |
| 4,404,272 | 9/1983 | Stahlhofen | 430/192 |
| 4,499,171 | 2/1985 | Hosaka et al. | 430/193 |
| 4,576,901 | 3/1986 | Stahlhofen | 430/325 |
| 4,581,321 | 4/1986 | Stahlhofen | 430/325 |
| 4,588,670 | 5/1986 | Kelly et al. | 530/165 |
| 4,818,658 | 4/1989 | Martin et al. | 430/156 |
| 4,929,536 | 5/1990 | Spak et al. | 430/193 |
| 4,931,381 | 6/1990 | Spak et al. | 430/192 |
| 4,931,549 | 6/1990 | Berner | 534/556 |

FOREIGN PATENT DOCUMENTS

| | | | |
|---|---|---|---|
| 1228066 | 10/1987 | Canada | 430/193 |
| 0140273 | 5/1985 | European Pat. Off. | |
| 0178356 | 4/1986 | European Pat. Off. | |
| 0212482 | 3/1987 | European Pat. Off. | |
| 0283898 | 9/1988 | European Pat. Off. | |
| 0287750 | 10/1988 | European Pat. Off. | |
| 0312950 | 4/1989 | European Pat. Off. | |
| 171024 | 3/1904 | Fed. Rep. of Germany | |
| 871668 | 6/1950 | Fed. Rep. of Germany | 430/193 |
| 865410 | 2/1953 | Fed. Rep. of Germany | |
| 1062247 | 7/1959 | Fed. Rep. of Germany | 430/193 |
| 263982 | 1/1989 | Fed. Rep. of Germany | 534/556 |
| 63-27835 | 2/1988 | Japan | |
| 341071 | 10/1959 | Switzerland | |
| 711808 | 7/1954 | United Kingdom | 430/193 |
| 717321 | 10/1954 | United Kingdom | 430/165 |
| 819667 | 9/1959 | United Kingdom | 430/193 |
| 2082339 | 3/1982 | United Kingdom | |

OTHER PUBLICATIONS

MacDonald et al., "Image Reversal: The Production of a Negative Image in a Positive Photoresist," IBM Research Disclosure, 1982; pp. 114–117.

Alling et al., "Image Reversal of Positive Photoresist, A New Tool for Advacing Integrated Circuit Fabrication," Proceedings of the SPIE, vol. 539, 1985, pp. 194–218.

Fierz-David et al., Helv. chim. acta 30, 1947, pp. 830–833.

W. Huber, Helv. chim. acta. 15, 1932, pp. 1372–1383.

Fierz-David, "Grundlegende Operationen der Farbenchemie" (Basic operations of dyestuff chemistry), 7th ed., 1947, pp. 172–175 and 250–253.

Bucherer, "Aus dem Laboratorium für Farbenchemie und Färberei-Technik der Technischen Hochschule zu Dresden," J. pr. Chemie 1904 (2) pp. 48, 78–83.

Houben-Weyl, vol. 6/I c, pp. 241–245.

Houben-Weyl, vol. 11/1, pp. 457–463.

Witt et al., Ber, 1891, vol. 24, pp. 3157–3163.

Anilin- und Extrakt-Fabriken, Basel, Chem. Zentralblatt 77, 1906, pp. 474–477.

Schmidt et a., Ber. 1931, 64, pp. 767, 772–773.

Knop et al., "Chemistry and Application of Phenolic Resins," Springer-Verlag, New York (Chapter 4), 1979, pp. 60–66.

Primary Examiner—Charles L. Bowers, Jr.
Assistant Examiner—John S. Chu
Attorney, Agent, or Firm—Foley & Lardner

[57] ABSTRACT

The invention relates to novel radiation-sensitive compounds which are esters or amides of a 1,2-naphthoquinone-(2)-diazide-4-sulfonic acid of the general formula

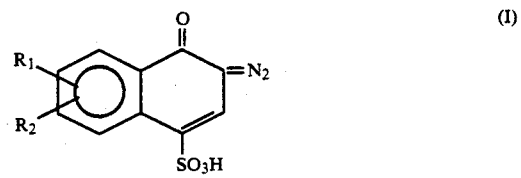

in which
R$_1$ and R$_2$ are identical or different and denote hydrogen, an alkyl group, an alkyl ether group or an alkyl thioether group whose carbon chains may be interrupted by ether oxygen atoms, an acylamino group, carboxylic acid ester group, sulfonic acid ester group or sulfonamide group,
R$_1$ and R$_2$ not being hydrogen at the same time.

The compounds are used as radiation-sensitive components in radiation-sensitive mixtures with which corresponding copying materials can be produced. The compounds have an absorption which is directed towards longer wavelengths matching the emission range of commercially available radiation sources. They also make it possible, in a reliable and practical manner, to carry out negativeworking image reversal processes.

25 Claims, No Drawings

RADIATION-SENSITIVE COMPOUNDS, RADIATION-SENSITIVE MIXTURE PREPARED THEREWITH AND COPYING MATERIAL

BACKGROUND OF THE INVENTION

The present invention relates to novel radiation-sensitive compounds, and a mixture prepared therewith, in particular a photoresist mixture. The mixture comprises a water-insoluble resinous binder which is soluble, or at least swellable, in aqueous alkaline or organic solvents, optionally an acid-activable crosslinking agent and an ester or an amide of a substituted 1,2-naphthoquinone-(2)-diazide-4-sulfonic acid as a radiation-sensitive compound. The invention further relates to a copying material which is prepared from a coating base and from the radiation-sensitive mixture. The copying material may optionally be used for producing positive or negative relief copies of a master or also for a combination thereof.

It is known that normally positive-working copying materials based on 1,2-benzoquinone- and 1,2-naphthoquinone-(2)-diazide-sulfonic acid derivatives also yield negative relief images as a result of a polarity reversal while maintaining a certain sequence of processing steps. The preparation and processing of such copying materials is described, for example, in U.S. Pat. No. 3,264,104, GB-A-2,082,339, DE-A-2,529,054, corresponding to U.S. Pat. No. 4,104,070, DE-A-3,325,022, corresponding to U.S. Pat. No. 4,581,321, and EP-A-0,212,482.

The photosensitive coating of the known copying materials is essentially composed of alkali-soluble cresol-formaldehyde novolak resins in combination with photosensitive substances such as 1,2-benzo- or 1,2-naphthoquinone-(2)-diazide derivatives. Resins and photosensitive compounds are dissolved in an organic solvent or solvent mixture and deposited in a thin coating on a coating base suitable for the particular application. Although the resin components of these resist mixtures are soluble in aqueous alkaline solutions, the photosensitive 1,2-quinonediazide compounds have a solution-inhibiting effect on the resin. On exposing the coated base to an image with actinic radiation, the photosensitive compound undergoes a structural change due to the irradiation, as a result of which the exposed regions of the coating become more soluble than the unexposed regions. Because of this solubility difference, the exposed regions of the copying layer dissolve in alkaline developer solution, while the unexposed regions remain essentially unchanged and intact so that a positive relief image of the master is produced on the coating base.

In most cases, the exposed and developed copying material is furthermore treated with an etchant, the regions of the copying layer which have not been stripped off by the developer protecting the coating base against the etchant. In this way, an etched image which corresponds in its polarity to the mask, template or other master used during exposure is produced on the coating base.

In a specific embodiment of a negative-working copying layer, for example a photoresist, based on 1,2-quinonediazide compounds, the light-affected regions of the coating are "cured" by crosslinking of the resin molecules after exposure to an image and subsequent heat treatment. The resin components are cured as a rule by a "crosslinking agent" which is incorporated in the coating and which is activated by the acid produced during the exposure of the 1,2-quinonediazide and by the heat treatment. The temperatures used in heating are below the decomposition temperature of the 1,2-quinonediazide. The heating may be carried out by irradiation, convection, by contact with heated surfaces, for example rollers, or by immersion in a heated bath of an inert liquid, for example water. The temperature may be between 100° and 150° C., preferably between 90° and 130° C.

Effective crosslinking agents are in general compounds which are easily able to form a carbonium ion under the acid and temperature conditions described. Examples thereof are the hexamethylol melamine ethers in accordance with DE-A-3,325,022, corresponding to U.S. Pat. No. 4,581,321, and also the compounds, proposed in EP-A-0,212,482, containing two or more hydroxyl or alkoxymethyl groups in aromatic molecular structures such as 1,4-bishydroxymethylbenzene or 4,4'-bismethoxymethyldiphenyl ether. 2,6-Dimethylol-p-cresol in accordance with U.S. Pat. No. 4,404,272 is also known as a crosslinking agent.

After the heat treatment, the photoresist coating is as a rule subjected to a total exposure ("flood exposure") in order to convert the still photosensitive coating regions completely into an alkali-soluble form. The flood exposure may in general be carried out under the same light source which was also used for the exposure to image.

Following the flood exposure, development is carried out with an aqueous alkaline developer solution which is normally also used in the case of a positive-working photoresist, for example aqueous solutions of sodium hydroxide, tetramethylammonium hydroxide, trimethylhydroxyethylammonium hydroxide, alkali phosphates, alkali silicates or alkali carbonates, which may contain wetting agents or small amounts of organic solvents. The development washes out the coating regions which were not affected by light in the original exposure to an image (negative copying material).

In the case of positive-working copying layers of the same coating composition in which the curing process has not been set in operation by the appropriate procedure, on the other hand, the coating regions exposed during the exposure to an image are washed out by the developer (positive copying material).

In most cases, the exposed and developed coating base is furthermore treated with an etchant, the copying layer remaining behind on the coating base having a protective function, depending on the processing method. The etchant is therefore able to act only on the coating-free regions of the coating base. An etched image, which in the case of a positive-working copying layer corresponds to the polarity of the exposure mask or, in the case of a negative-working copying layer reverses the polarity of the exposure mask, is produced in this way on the coating base.

The positive or negative relief image of the copying layer produced by the above-described processing methods on the coating base is suitable for various applications, for example as an exposure mask or as an image in the production of semi-conductor components in microelectronics, as a printing form for letterpress, gravure or lithographic printing, and also for the production of nickel rotary cylinders by electroplating.

Important criteria used to assess the suitability of a copying layer, for example a photoresist, for commercial purposes are, inter alia: the photosensitivity, the development and image contrast, the resist resolution and the adhesion of the resist to the coating base.

High photosensitivity is important for a photoresist, in particular, if it is used for applications in which several exposures are necessary, for example in the production of multiple images in a repetitive method or in those cases where light of lower intensity is used, for example in projection exposure procedures in which the light is passed through a series of lenses and monochromatic filters, as in the case of projection exposure units ("steppers") which employ monochromatic light.

The development contrast is a measure of the ability of a photoresist to transmit the dimensions of the mask reliably and precisely through the entire thickness of the coating. In the ideal case, the dimensions at the top of the coating are precisely the same dimensions as those at its bottom. A photoresist with improved contrast therefore has steeper edges.

The resist resolution relates to the ability of a photoresist system to reproduce even the finest lines and spaces of a mask used for the exposure, the exposed and developed regions having a high degree of edge steepness and edge sharpness.

In many technical fields of application, in particular in the production of semiconductor components in microelectronics, the photoresist employed has to have a particularly high resolving power if it is required to reproduce very small line widths and space widths (approx. 1 $\mu$m). This property the ability to reproduce superfine dimensions in the order of magnitude of 1 $\mu$m and less—is of the greatest importance for the large-scale production of integrated circuits on silicon chips and similar components. If photographic methods are used, the integration density on such a chip can be improved only by increasing the resolving power of the photoresist. The miniaturization of microprocessors and other semi-conductor components in microelectronics makes it necessary to use those methods which proceed as rapidly, reliably and simply as possible and yield reproducible results for structuring suitable substrates.

The specialist and patent literature proposes methods which make it possible to produce negative resist relief images with photoresist coatings based on 1,2-quinonediazide derivatives using a particular procedure, such as S. A. MacDonald et al., "Image Reversal: The Production of a Negative Image in a Positive Photoresist", page 114, IBM Research Disclosure, 1982; E. Alling et al., "Image Reversal of Positive Photoresist. A new Tool for Advancing Integrated Circuit Fabrication", Proceedings of the SPIE, Vol. 539, page 194, 1985; U.S. Pat. No. 4,104,070 and U.S. Pat. No. 4,576,901.

The technical implementation of these known image reversal methods is in some cases very complicated and therefore not practicable for photoresist processing in microelectronics. The quality of the resist structures is in most cases not reliably reproducible. In addition, a disadvantage is that, to carry out the reversal process, in some methods an amine gasification of the photoresist coating which can be controlled technologically only with difficulty is necessary or additives have to be incorporated in the photoresist coating which appreciably reduce the shelf life.

It is also known that the resolving power of a photoresist based on 1,2-quinonediazide derivatives is better by approx. 0.2–0.3 $\mu$m in an image reversal method than in a positive procedure.

EP-A-0,212,482 proposes a method of producing negative relief image structures from a positive-working copying material which essentially contains a water-insoluble resin which is soluble in alkaline solvents, a 1,2-quinone-(2)-diazide-4-sulfonic acid ester as a photosensitive compound and a cross-linking agent which functions in the presence of acid. Due to the composition of the coating and to the course of the process in producing negative relief image structures, some of the disadvantages of the known earlier methods are eliminated, such as, for example, fewer process steps, no treatment with substances with an alkaline reaction or which form salts, no use of particularly high-energy exposure sources such as, for example, electron beams. A disadvantage is, however, that the photosensitive coating proposed in EP-A-0,212,482 is primarily suitable for exposure in the middle UV range (313–365 nm) and for i-line exposure (365 nm).

The Japanese Published Specification 27,835/88 discloses aryl esters of halogen-substituted naphthoquinonediazide sulfonic acids which can be used for photoresist materials. They are basically suitable for light of the wavelength $\lambda = 365$ nm and broad-band exposure with mercury high-pressure lamps. The light sensitivity for 436 nm exposure is very low and not realistic. They are suitable, in particular, for resist formulations sensitive to electron beams in which halogen-substituted compounds prove to be particularly advantageous.

Only a few useable exposure units (i-line steppers) are available for the 365 nm exposure since the technological requirements for this still have not been ideally solved. In contrast to this, g-line exposure (436 nm) is very predominantly employed at present in microlithography. The overwhelming majority of exposure units for high resolution (g-line steppers) are designed for this wavelength. There is therefore an urgent need to improve the resolving potential in the case of g-line exposure without capital-intensive installation of steppers which operate at shorter wavelength. This is possible with an image reversal method.

The solution route found for i-line exposure (365 nm) is, however, not practicable for g-line exposure (436 nm). The photosensitivity of these known resists is very low at 436 nm, which manifests itself in longer, unrealistic exposure times and the poorer development contrast and image contrast and lower microstructure resolving power associated therewith.

SUMMARY OF THE INVENTION

Accordingly, it is an object of the present invention to provide an image-reversible photoresist which has an adequate photosensitivity at 436 nm.

Another object of the present invention is to provide an image-reversible photoresist which permits the use of the g-line stepper for producing a further generation of memory components having 0.2–0.3 $\mu$m smaller structure dimensions.

In accomplishing the foregoing objectives, there has been provided, in accordance with one aspect of the present invention, a radiation-sensitive compound which is an ester or amide of a 1,2-naphthoquinone-(2)-diazide-4-sulfonic acid of the general formula:

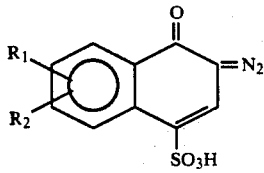

(I)

in which

R₁ and R₂ are identical or different and denote hydrogen, alkyl, an alkyl ether group or an alkyl thioether group whose carbon chains may be interrupted by ether oxygen atoms, an acylamino group, carboxylic acid ester group, sulfonic acid ester group or sulfonamide group, R₁ and R₂ not being hydrogen at the same time.

In accordance with another aspect of the present invention there is provided a radiation-sensitive mixture comprising a water-insoluble resinous binder which is soluble, or at least swellable, in aqueous alkaline or organic solvents, optionally a crosslinking agent and a radiation-sensitive compound or a mixture of radiation-sensitive compounds, wherein at least one of the radiation-sensitive compounds is an ester or amide as described above.

In accordance with a further aspect of the present invention there is provided a radiation-sensitive copying material comprising a base and a radiation-sensitive coating comprising the above-described mixture essentially free of solvent.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF PREFERRED EMBODIMENTS

Preferably, compounds are proposed according to the general formula I, in which

R₁ and R₂ are identical or different with the above-mentioned restriction and denote hydrogen, alkyl containing 1 to 6 carbon atoms, an alkyl ether group or an alkyl thioether group whose carbon chains may be interrupted by ether oxygen atoms, containing a total of 1 to 6 carbon atoms, or an acylamino group containing 2 to 6 carbon atoms.

In particular, compounds are suitable in which

R₁ denotes hydrogen and

R₂ denotes alkyl ether groups or alkyl thioether groups whose carbon chain may be interrupted by ether oxygen atoms, containing 1 to 6 carbon atoms.

Compounds in which

R₁ denotes hydrogen or methyl, and

R₂ denotes methyl or an alkyl ether group containing 1 to 4 carbon atoms have proved to be very particularly satisfactory.

Specific compounds are those in which

R₁ denotes, in position 6, hydrogen or methyl and

R₂ denotes, in position 7, methyl or the methyl ether group, very preferably those in which R₁ denotes, in position 6, hydrogen, and R₂ denotes, in position 7, the methyl ether group.

The invention achieves the result of shifting towards longer wavelengths the absorption of the radiation-sensitive esters or amides from the 1,2-naphthoquinone-(2)-diazide series which can be prepared with the compounds according to the invention, the formation of a fairly strong acid during the photoreaction being maintained at the same time. In spite of the shifting of the absorption peak towards longer wavelengths, the compounds of the present invention still have a sufficiently high absorption, even when subjected to i-line exposure (λ=365 nm). Although the overlapping of the absorption ranges of the photoactive compound with the emission range of the radiation source is a necessary condition for the occurrence of a photoreaction, the fulfilment of this condition alone is still not sufficient to cause the desired photoreaction also to proceed in reality.

Surprisingly, it was, however, possible to find substitution patterns from the series comprising the 1,2-naphthoquinone-(2)-diazide-4-sulfonic acid derivatives, which substitution patterns also make it possible to carry out negative-working image reversal processes highly efficiently and with a reliable and technically practicable procedure.

Possible esters are the reaction products of the 1,2-naphthoquinone-(2)-diazide-4-sulfonic acids I or their chlorides with aliphatic or aromatic mono- or polyhydroxyl compounds. Preferred are the reaction products containing mono- or polyfunctional phenol derivatives of the general formulae II, III and IV;

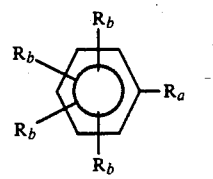

(II)

in which

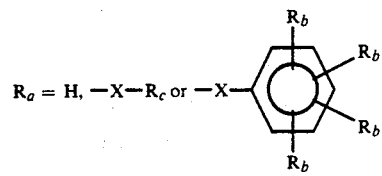

$R_b$=H, an OH group, halogen or a lower alkyl group, at least one and not more than six $R_b$ groups being OH groups, X=a carbon bond, —O—, —S—, —SO₂—,

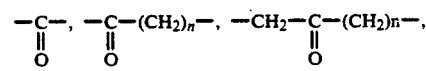

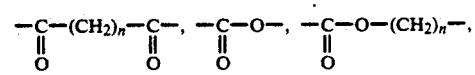

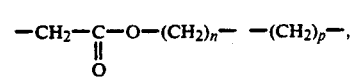

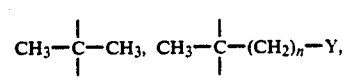

-continued

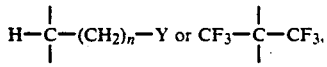

it being possible in each case for individual CH$_2$ groups to be replaced by ether functions or the hydrogen by substituents, n=1 or 2,
p=1 to 3,
Y=H or an optionally substituted alkoxy group, carboxy group, carboxyalkyl group, carboxyalkoxyalkyl group or aryl group, and
R$_c$=H or an optionally substituted alkyl group or aryl group,
or of the formula III

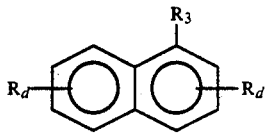

(III)

in which

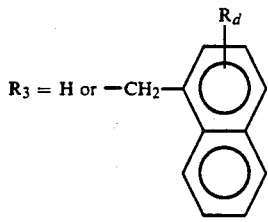

and

R$_d$=H or an OH group, at least one of the R$_d$ groups being an OH group,
or of the formula IV

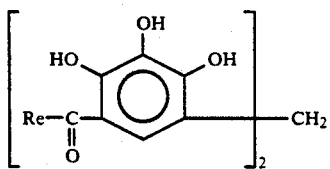

(IV)

in which
R$_e$=H or an optionally substituted alkyl group, alkoxy group or aryl group,
or of the formula V R$_f$—OH (V)

in which
R$_f$=a straight-chain or branched alkyl group, cycloalkyl group or aralkyl group optionally substituted by halogen or an acylamino radical and containing 1 to 14 carbon atoms, whose carbon chain may be interrupted by ether oxygen atoms, or the group —Z—OH in which
Z=an alkylene radical containing 2 to 12 carbon atoms or a cycloalkylene radical containing 8 to 18 carbon atoms, whose carbon chains may be interrupted by ether oxygen atoms, or an aralkylene radical containing 8 to 16 carbon atoms, it being possible for the cycloaliphatic and aromatic members to be joined by a single bond, by —O—, —S—, —SO$_2$—, —CO—,

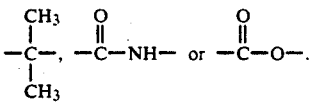

The preferred phenol derivatives include, for example, benzene compounds carrying hydroxyl groups such as 1,2-dihydroxybenzene, 1,3-dihydroxybenzene, 1,4-dihydroxybenzene, 1,2,3-trihydroxybenzene, 1,2,4-trihydroxybenzene, 1,3,5-trihydroxybenzene etc.;

dihydroxybenzophenones such as 2,2'-dihydroxybenzophenone, 2,3'-dihydroxybenzophenone, 2,4-dihydroxybenzophenone, 2,4'-dihydroxybenzophenone, 2,5-dihydroxybenzophenone, 3,3'-dihydroxybenzophenone, 4,4'-dihydroxybenzophenone etc.;

trihydroxybenzophenones such as 2,2',6-trihydroxybenzophenone, 2,3,4-trihydroxybenzophenone, 2,4,4'-trihydroxybenzophenone, 2,4,6-trihydroxybenzophenone, 3,4,5-trihydroxybenzophenone etc.;

tetrahydroxybenzophenones such as, for example, 2,2',3,4-tetrahydroxybenzophenone, 2,2',4,4'-tetrahydroxybenzophenone, 2,2',4,6'-tetrahydroxybenzophenone, 2,2',5,6'-tetrahydroxybenzophenone, 2,3',4,4'-tetrahydroxybenzophenone, 2,3',4,6-tetrahydroxybenzophenone, 2,4,4',6-tetrahydroxybenzophenone, 3,3',4,4'-tetrahydroxybenzophenone etc.;

pentahydroxybenzophenones; hexahydroxybenzophenones; dihydroxy- and trihydroxyphenyl alkyl ketones such as 2,4-dihydroxyphenyl alkyl ketones, 2,5-dihydroxyphenyl alkyl ketones, 3,4-dihydroxyphenyl alkyl ketones, 3,5-dihydroxyphenyl alkyl ketones, 2,3,4-trihydroxyphenyl alkyl ketones, 3,4,5-trihydroxyphenyl alkyl ketones, 2,4,6-trihydroxyphenyl alkyl ketones, etc.; alkyl groups containing 1 to 12 carbon atoms, which are optionally branched, such as, for example methyl, ethyl, butyl, n-hexyl, heptyl, decyl, dodecyl etc. preferably being used;

dihydroxyphenyl aralkyl ketones; trihydroxyphenyl aralkyl ketones; dihydroxydiphenyls; trihydroxydiphenyls such as 2,2',4-trihydroxydiphenyl; tetrahydroxydiphenyls such as, for example, 2,2',4,4'-tetrahydroxydiphenyl; dihydroxydiphenyl ether; dihydroxydibenzyl ether; dihydroxydiphenyl alkanes, preferably with low alkylene chains such as, for example, methylene, ethylene, propylene etc.; dihydroxybenzoic acid; trihydroxybenzoic acids; alkyl dihydroxy- and trihydroxybenzoates, the alkyl group preferably having 1 to 12 carbon atoms, example, n-butyl 2,4-, 2,5-, 3,4- and 3,5-dihydroxybenzoate, 2,4,4-trimethylpentyl 2,4-dihydroxybenzoate, etc.; phenyl dihydroxy- and trihydroxybenzoates; dihydroxy-, trihydroxy- and tetrahydroxydiphenyl sulfides such as, for example, 4,4'-dihydroxydiphenyl sulfide; dihydroxydiphenyl sulfones; dihydroxy- and trihydroxyphenyl naphthyl ketones such as, for example, 2,3,4-trihydroxyphenyl 1-naphthyl ketone and similar compounds.

The compounds of the general formula II in which at least one R' group is a halogen atom or a lower alkyl group include, for example, 2,4-dihydroxy-3,5-dibromobenzophenone, 5-bromo-2,4-dihydroxybenzoic acid and its esters, 2,4,2',4'-tetrahydroxy-3,5,3',5'-tetrabromodiphenyl, 4,4'-dihydroxy-2,2'-dimethyl-5,5'-di-tert-butyldiphenyl, 4,4'-dihydroxy-2,2'-dimethyl-5,5'-di-tert-butyldiphenyl sulfide, 2,4,2',4'-tetrahydroxy- 3,5,3′,5′-tetrabromodiphenyl sulfone and similar compounds. The benzophenones containing hydroxyl groups, in particular the trihydroxybenzophenones, are preferably used as phenol compounds of the general formula II.

The phenol compounds of the general formula III preferably include the following compounds: dihydroxynaphthalenes, such as 1,2-dihydroxynaphthalene, 1,4-dihydroxynaphthalene, 1,5-dihydrodihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene etc.; dihydroxydinaphthylmethanes such as 2,2′-dihydroxydinaphthylmethane etc.

The dihydroxynaphthalenes are preferably used. The hydroxyl groups of the dihydroxynaphthalenes may, moreover, be situated either on one nucleus or on both nuclei of the naphthalene molecule.

The phenol compounds of the general formula IV preferably include the following compounds: bis(3-benzoyl-4,5,6-trihydroxyphenyl)methane, bis(3-acetyl-4,5,6-trihydroxyphenyl)methane, bis(3-propionyl-4,5,6-trihydroxyphenyl)methane, bis(3-butyryl-4,5,6-trihydroxyphenyl)methane, bis(3-hexanoyl-4,5,6-trihydroxyphenyl)methane, bis(3-heptanoyl-4,5,6-trihydroxyphenyl)methane, bis(3-decanoyl-4,5,6-trihydroxyphenyl)methane, bis(3-octadecanoyl-4,5,6-trihydroxyphenyl)methane etc.

In addition, possible esters are the reaction products of the 1,2-naphthoquinone-(2)-diazide-4-sulfonic acids I or their chlorides with mono- or dihydric alcohols of the general formula V.

The mono- or dihydric alcohols of the general formula V preferably include, for example, n-butyl alcohol, sec-butyl alcohol, n-amyl alcohol, n-octyl alcohol, n-dodecyl alcohol, lauryl alcohol, myristyl alcohol, cyclohexanol, benzyl alcohol, β-phenylethyl alcohol, di-, tri-, tetraethylene glycol, 1,4-dihydroxycyclohexane.

As amides, use may be made of the reaction products of the 1,2-naphthoquinone-(2)-diazide-4-sulfonic acids I or their chlorides with aromatic or aliphatic primary or secondary amines of the general formula VI:

$$H—NR_gR_h \qquad (VI)$$

in which

$R_g$=hydrogen, an optionally substituted alkyl, cycloalkyl, aryl or aralkyl radical containing 1 to 14 carbon atoms whose carbon chain may be interrupted by ether oxygen atoms,

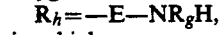$R_h$=—E—$NR_gH$, in which

E=an alkylene radical containing 2 to 12 carbon atoms whose carbon chain may be interrupted by ether oxygen atoms, a cycloalkylene, arylene or aralkylene radical containing 8 to 18 carbon atoms, it being possible, in the case of polynuclear compounds, for the cycloaliphatic and aromatic members to be joined by a single bond, by —O—, —S—, —$SO_2$—, —CO— or —$R_g$—.

Preferably, these are longer-chain aliphatic amines whose carbon chain may be interrupted by oxygen atoms, or cyclic or aromatic amines such as n-hexylamine, laurylamine, cyclohexylamine, cyclododecylamine, o-, p-, m-toluidine, o-, p-anisidine, p-phenetidine, 1,6-diamino-n-hexane, 1,10-diamino-n-decane, o-, p-, m-phenylenediamine, 4,4′-diaminodiphenyl ether, 4,4′-bis(aminomethyl)diphenyl ether, 1,4-bis(aminomethyl)benzene, 1,4-bis(propylaminomethyl)diphenyl ether, 4,4′-bis(sec-butylaminomethyl)diphenyl ether, 1,4-bis(n-octylamino)cyclohexane, 1,4-bis(sec-butylamino)cyclohexane, 4,4′-bis(2-methoxyethylaminomethyl)diphenyl ether, 4,4′-bis(2-phenylethylaminomethyl)diphenyl ether.

The preparation of radiation-sensitive esters from the series comprising the naphthoquinonediazides is known and is described by way of example in U.S. Pat. Nos. 3,046,118, 4,397,937 and EP-A-0,140,273, and that of radiation-sensitive amides in DE-C-865,410. The radiation-sensitive esters and amides in accordance with the invention are prepared by analogy with these methods from the chlorides of the 1,2-naphthoquinone-(2)-diazide-4-sulfonic acids I by reaction with a hydroxyl compound of the type II to V or an amino compound of the type VI, as a rule in the presence of an acid acceptor.

Suitable solvents for carrying out the reaction are: acetone, tetrahydrofuran, methylene chloride, pyridine etc. The acid acceptor may be inorganic, such as, for example sodium carbonate, or organic, such as a sodium salt of a weak organic acid, a tertiary amine, for example triethylamine or N-methylmorpholine.

The radiation-sensitive compounds obtained in this manner may be additionally purified if necessary.

The 1,2-naphthoquinone-(2)-diazide-4-sulfonic acids of the general formula I which are used as starting substances for preparing the radiation-sensitive esters and amides in accordance with the invention are listed in Table 1 of the appendix. Their preparation proceeds through a plurality of intermediate steps, some of which are described in the literature[1)] or were synthesized by analogy with methods known in the literature. A method for preparing similar compounds is disclosed in German Patent Application reference P 38 37 499.4, corresponding to U.S. application Ser. No. 07/431,182 filed Nov. 3, 1989, now U.S. Pat. No. 5,082,932 issued Jan. 21, 1992.

[1)] References

1) H. E. Fierz-David et al., Helv. chim. acta 30, 831 ff. (1947)

2) W. Huber, Helv. chim. acta. 15, 1372 (1932)

3) H. E. Fierz-David, "Grundlegende Operationen der Farbenchemie" ("Basic operations of dyestuff chemistry"), 7th ed. p. 172–175 (1947) and p. 251–252

4) H. T. Bucherer, J. pr. Chemie 1904 (2), 69, 49 ff.

5) Houben-Weyl, vol. 6/I c, 241 ff. and vol. 11/1, 457 ff.

6) Witt and Kaufmann, Ber. 1891, 24, 3157 ff.

7) Anilin- und Extrakt-Fabriken, Basel, Chem. Zentralblatt 77, 474–477 (1906)

8) J. Schmidt and W. Maier, Ber. 1931, 64, 767 ff.

Thus, for example, 6-methoxy- and 7-methoxy-1,2-naphthoquinone-(2)-diazide-4-sulfonic acid are obtained from commercially available 1-acetylamino-6-naphthol or 1-acetylamino-7-naphthol (BAYER AG) respectively, and 8-methoxy-1,2-naphthoquinone-(2)-diazide-4-sulfonic acid from commercially available 1-amino-8-naphthol-4-sulfonic acid (BAYER AG) in 7-step reaction sequences in each case.

The invention also relates to a radiation-sensitive mixture which contains a water-insoluble resinous binder which is soluble, or at least swellable, in aqueous alkaline or organic solvents, optionally a crosslinking agent and also a radiation-sensitive compound or a mixture of radiation-sensitive compounds, wherein at least one of the radiation-sensitive compounds is an ester or an amide as disclosed herein.

The radiation-sensitive mixture, in particular photoresists, according to the invention are prepared by mixing the radiation-sensitive compounds with the alkali-soluble binders, solvents and, optionally, further additives. Suitable alkali-soluble binders are, for example, phenol-resin and cresol-resin novolaks, polyvinylphenol or polyvinylalkylphenol resins.

The alkali-soluble novolaks and polyvinylphenol resins which can be used for preparing photosensitive mixtures are known. A method of preparing such novolaks is described in "Chemistry and Application of Phenolic Resins" by A. Knop and W. Scheib, Springer Verlag, New York, 1979, Chapter 4. The use of polyvinylphenols is known, for example, from U.S. Pat. No. 3,869,292.

To prepare the mixture according to the invention, the novolak or the polyvinylphenol and the radiation-sensitive compound are dissolved in a solvent. Suitable solvents for this are, for example, glycol ethers such as ethylene glycol monomethyl ether and ethylene glycol monoethyl ether or also their acetates, for instance propylene glycol methyl ether acetate; esters such as ethyl acetate and butyl acetate; ketones such as methyl ethyl ketone, cyclopentanone and cyclohexanone; and also aromatic hydrocarbons such as toluene and xylene. Mixtures of these solvents may also be used. The use of the solvent or solvent mixture depends in the individual case on, inter alia, the particular coating method, the desired coating thickness, the drying conditions, the solubility of the individual components and the rate of evaporation of the solvent after coating the coating base with the photoresist mixture.

Before being deposited on a coating base, further additives such as, for example, colorants, dyestuffs, leveling agents, plasticizers, adhesion promoters, development accelerators, surfactants such as nonionic surfactants, and crosslinking agents may be added to the radiation-sensitive mixture according to the invention.

In a preferred embodiment, the content of solid constituents in the radiation-sensitive mixture is about 15 to 99 percent by weight for the alkali-soluble binder, and about 1 to 85 percent by weight for the radiation-sensitive compound. In particular, the mixture contains the binder in a proportion of about 50 to 97 percent by weight, and very particularly preferably, of about 65 to 93 percent by weight, based on the weight of the solid constituents. The proportion of radiation-sensitive compound is, in particular, about 3 to 50 percent by weight and very particularly preferably, about 7 to 35 percent by weight, based on the weight of the solid constituents of the mixture. To prepare the mixture, the binder and the radiation-sensitive compound are mixed with the solvent in a manner such that the solvent is present in a proportion of about 40 to 90, preferably of about 60 to 85, percent by weight, and in particular of about 65 to 80 percent by weight, in each case based on the weight of the total mixture.

Dyestuffs which can be used as additives for the mixtures according to the invention are, for example, methyl violet 2B (C.I. 42,535), crystal violet (C.I. 42,555), malachite green (C.I. 42,000), victoria blue B (C.I. 44,045) and neutral red (C.I. 50,040), and also coumarin dyestuffs and dyestuffs in accordance with the German Patent Application reference P 37 35 852.9, corresponding to U.S. application Ser. No. 260,307. These dyestuffs are added in an amount of 1 to 10 percent by weight, based on the solid constituents of the mixture. The dyestuff added reduces the back scattering of light from the coating base and thus contributes to an improved resolution.

Leveling agents may be used in an amount of up to 5 percent by weight, based on the combined weight of binder and radiation-sensitive compound.

Suitable plasticizers are, for example, tri($\beta$-chloroethyl) phosphate, stearic acid, dicamphor, polypropylene, acetal resins, phenoxy resins and alkyde resins, which may be added in proportions of about 1 to 10 percent by weight, based on the combined weight of binder and radiation-sensitive compound. The plasticizer added improves the coating properties of the mixture and makes possible application in a smooth and uniformly thick coating to the coating base.

Suitable adhesion promoters for improving the adhesion of the mixture to the coating base are specific organosilicon compounds in a proportion of up to about 4 percent by weight, based on the combined weight of binder and radiation-sensitive compound.

As development accelerators, it is possible to add, for example, aromatic carboxylic acids or polyhydroxyl compounds in a proportion of up to about 20 percent by weight, based on the combined weight of binder and radiation-sensitive compound. These accelerators result in the solubility of the radiation-sensitive coating increasing both in the exposed and also in the unexposed regions. They are therefore used in those applications in which the development rate is primarily of importance. While the exposed regions of the photoresist coating are dissolved more rapidly by the developer when accelerators have been added, the development accelerators also at the same time bring about, however, a greater loss of photoresist coating from the unexposed regions, with the result that a certain degree of contrast may be lost.

As nonionic surfactants, use may be made, for example, of nonylphenoxypoly(ethylenoxy)ethanol, octylphenoxy(ethylenoxy)ethanol, and dinonylphenoxypoly(ethylenoxy)ethanol in a proportion of up to 10 percent by weight, based on the combined weight of the binder and radiation-sensitive compound.

Suitable crosslinking agents which are in general added to a radiation-sensitive mixture which is intended for a negative-working photoresist are described in EP-A-0,212,482 and U.S. Pat. No. 4,404,272. These are mainly compounds from the aromatic series containing two or more hydroxyl or alkoxymethyl groups in the molecule, such as 1,2-bishydroxymethylbenzene, 1,4-bismethoxymethylbenzene, 2,5-bis(hydroxymethyl)furan, 2,6-bishydroxymethyl-4-methylanisole, 1,4-bis($\alpha$-hydroxybenzyl)benzene 2,5-dimethyl-1,4-bishydroxymethylbenzene, 4,4'-bishydroxymethyldiphenyl ether, 4,4'-bismethoxydiphenyl, 2,6-bishydroxymethyl-4-methoxy- or -4-ethoxyphenol, 4,4'-bismethoxymethyldiphenyl ether and epoxy-cresol novolak resins, and also alkoxymethylmelamine derivatives. Particularly preferred are: 2,6-bishydroxymethyl-4-methyl-, -4-ethyl-, -4-propyl-, -4-isopropyl-, -4-n-butyl-, -4-tertbutyl-, and -4-(2-phenyl-2-propyl)phenol. The crosslinking agents may be used in amounts of about 1.5 to 20 percent by weight, preferably of 3 to 12 percent by weight, based on the solids content.

In the presence of acids and at elevated temperature, the binder molecules are crosslinked by these compounds, i.e., the radiation-sensitive coating is cured. The acid necessary for curing the coating is produced as a consequence of the photoreaction of the radiation-sensitive compound.

According to the invention, a radiation-sensitive copying material is furthermore proposed which comprises the above-described radiation-sensitive mixture, which is essentially freed of solvents, and a coating base.

The radiation-sensitive mixture may be deposited on the coating base by one of the methods usual in photoresist coating such as immersion, spraying or spinning-on. In the case of spinning-on, the percentage proportion of solids in the resist solution may, for example, be adjusted in a manner such that, depending on the spinning-on equipment used in the individual case and on the time interval adopted for the spinning-on operation, a coating is produced in the desired thickness. Suitable base materials are, by way of example: silicon, aluminum, polymeric resins, silicon dioxide, doped silicon dioxide, silicon nitride, tantalum, copper, polysilicon, ceramic and aluminum/copper alloys.

The radiation-sensitive mixtures prepared by the method described are suitable, in particular, for application to silicon wafers which carry a coating of silicon dioxide such as are used in the production of microprocessors and other semiconductor components used in microelectronics. Equally, a wafer of silicon on aluminum oxide may be used. The coating base may be composed of various polymeric resins, in particular of transparent polymers such as polyesters. In the case where the coating base is a silicon wafer or a gallium arsenide wafer, at least one further coating is preferably additionally deposited between the semiconducting material and the radiation-sensitive coating.

After the radiation-sensitive mixture has been applied to the coating base in the form of a wafer, the whole is subjected to a baking at about 80° to 105° C. This heat treatment is continued until the solvent has essentially evaporated and a thin coating of about 1 $\mu$m remains behind on the coating base.

The coated base is then irradiated in a known manner by means of actinic radiation, in particular UV light, for example of the wavelength $\lambda = 248$ or 365 nm, or shortwave visible light, for example of the wavelength $\lambda = 405$ or 436 nm, through suitable masks, negatives, templates etc., in accordance with an image, or is exposed to directed electron radiation or the radiation of a laser. The term "actinic radiation" covers both the x-ray range and electromagnetic radiation in the technically applicable wavelength range of $\lambda = 193$–450 nm, and electron radiation.

For the purpose of development, the copying materials which have been exposed to an image are immersed in an aqueous alkaline developer solution, the solution preferably being strongly agitated by blowing nitrogen through it. In industry, spray development processes are frequently used or the developer solution is deposited batchwise on the wafer (puddle development).

After removal from the developer solution, the material may be submitted to a heat post-treatment or baking treatment in order to increase the adhesion and the chemical resistance of the coating to etching solutions and other substances. The heat treatment after development may comprise an oven curing of coating and base at temperatures below the softening point of the coating.

For industrial applications, in particular in the production of semiconductor components on silicon bases having a silicon dioxide coating, the developed bases may be treated with a buffered etching solution based on hydrofluoric acid. The photoresist mixtures according to the invention are resistant to such acid-based etching solutions and ensure an effective protection of the unexposed areas of the base coated with the photoresist mixture.

The radiation-sensitive mixtures according to the invention are preferably suitable as photoresist mixtures. They may, however, also be used as radiation-sensitive mixtures for the production of printing plates or for color-proofing films.

If the copying material which has been produced by coating a coating base with the radiation-sensitive mixture according to the invention is used for the negative-working image reversal process, a second brief heat treatment is carried out at a temperature in the range between 90° and 150° C. after the exposure to an image using actinic radiation. During this heat treatment, the binder is cured in the exposed regions of the photoresist coating. The duration of the heat treatment is between about 10 and 90 seconds. After heat treating and cooling the copying material, the photoresist coating is developed or, preferably, exposed, before development, to UV irradiation over the entire surface (flood exposure). The developers used are aqueous alkaline solutions which may contain inorganic or quaternary organic bases, may be buffered or may contain additional additives (inter alia, wetting agents). In this process, the coating regions which were not affected by the radiation in the original image formation are washed out and the coating regions which were affected by the radiation are not attacked (negative process). A relief copy of the exposure mask is produced with altered polarity (negative copy).

Positive process and image reversal process may also be combined on one coating base (photocomposing).

PREPARATION OF THE PHOTOSENSITIVE COMPOUNDS

The following examples describe in more detail methods of preparing the compounds according to the invention and also their use in radiation-sensitive mixtures and copying materials.

The preparation of the compounds according to the invention from the 1,2-naphthoquinone-(2)-diazide-4-sulfonic acids I and the mono- or polyfunctional hydroxyl or amino compounds II–VI is achieved in 9 or 10 reaction stages.

A number of the novel esters and amides of the 1,2-naphthoquinone-(2)-diazide-4-sulfonic acids I (Table 1) which were synthesized and tested in mixtures as radiation-sensitive component are listed in Table 2 of the appendix. The numbering of the compounds from 1 to 19 is retained in the application examples. In Example 15, the molar extinction coefficients $\epsilon$ and the "standardized" molar extinction coefficients $\epsilon'$ of a number of the compounds listed in Table 2 are specified (in conjunction with Tables 4 and 5). The numbering is identical to that in Table 2.

Unless otherwise specified, percentage and quantity ratios are to be understood in weight units. Parts by weight (pbw) and parts by volume (pbv) are in the relationship of g to ml.

SYNTHESIS EXAMPLE 1

Synthesis of the aryl ester from 2,3,4-trihydroxybenzophenone and 7-methoxy-1,2-naphthoquinone-(2)-diazide-4-sulfonic acid

7-Methoxy-1-acetylaminonaphthalene (1st. Reaction staoe)

96 g of sodium hydroxide pellets are dissolved in 1100 ml of water and 300 g of 1-acetylamino-7-naphthol (95% strength) are then introduced into this solution at 20°-25° C. while stirring. 480 g of dimethyl sulfate are added dropwise to the resulting brown solution formed in the course of 1 hour, during which process the internal temperature rises to 35°-40° C. and the reaction product precipitates in finely crystalline form. Stirring of the reaction mixture is continued for 1 hour at 20°-25° C., then it is held for 30 minutes at internal temperature of 90°-100° C. and then cooled down, the almost colorless 7-methoxy-1 -acetylaminonaphthalene is filtered off by suction and dried in air at 20°-25° C.

Yield: 296 g (92% of theory)
M.p.: 157°-159° C.

7-Methoxy-1-aminonaphthalene hydrogensulfate (2nd. Reaction stage)

145 g of 7-methoxy-1-acetylaminonaphthalene are introduced into 670 ml of 20%-strength sulfuric acid while stirring and the suspension is slowly heated to boiling under reflux. After reaching the boiling point (100°-103° C.), this temperature is maintained for a further 3 hours, a dark-brown solution being formed. Then some oily, dark constituents are filtered off and 85 g of sodium hydrogensulfate are added to the still warm filtrate while stirring. The solution is allowed to cool to 10° C. and it is then kept for a further 2-3 hours at 0° C. The crystalline precipitate is filtered off by suction and pressed out well on a sintered disk filter funnel.

The 7-methoxy-1-aminonaphthalene hydrogen-sulfate, which is still moist from the sintered disk filter funnel, is dissolved in 650 ml of water at 90°-95° C., 10 g of sodium dithionite and 35 g of activated carbon are added to clarify the brown solution, the hot solution is filtered and the almost colorless filtrate is cooled to 0° C. After 2-3 hours, the precipitated colorless product is filtered off by suction, washed on the sintered disk filter funnel with ice water and pressed out well. The 7-methoxy-1-aminonaphthalene hydrogensulfate purified in this manner, which is still moist from the sintered disk filter funnel, is dried in a preliminary manner for 48 hours in air at 20°-25° C. and then dried further at 110° C. in a circulating-air drying oven.

Yield: 90 g (53% of theory)
Decomposition point: 175°-180° C. (dark coloration).

7-Methoxy-1-aminonaphthalene-4-sulfonic acid (3rd. Reaction stage)

50 g of purified and dried 7-methoxy-1-aminonaphthalene hydrogensulfate are heated for 6 hours at 160°-200° C. in vacuo (20 mm Hg) in a rotating reaction vessel (baking process). After cooling, the dark-brown, grainy reaction mixture is taken up in 1600 ml of 0.5%-strength sodium hydroxide solution at 80°-90° C. The brown solution, which contains some dark flaky constituents, is treated with 25 g of activated carbon, filtered and cooled to 50°-60° C. On adding 150 ml of glacial acetic acid while stirring, the 7-methoxy-1-aminonaphthalene-4-sulfonic acid precipitates as flakes with a pearly lustre. After cooling the suspension to 20°-25° C., the crystalline precipitate is filtered off by suction and dried in air at 20°-25° C.

Yield: 27 g (57.8% of theory)
M.p.: >250° C. (charring)

7-Methoxy-2-nitroso-1-naphthol-4-sulfonic acid (Na salt)

(4th. Reaction stage)

218 g of 7-methoxy-1-aminonaphthalene-4-sulfonic acid are dissolved at 20°-25° C. while stirring in sodium hydroxide solution prepared from 1575 ml of water and 34.5 g of sodium hydroxide, and 300 g of sodium disulfite ($Na_2S_2O_5$) are introduced into the brown solution formed, the sodium salt of the 7-methoxy-1-aminonaphthalene-4-sulfonic acid precipitating as colorless crystals and going into solution on heating the suspension. The solution is boiled for 20 hours (102°-105° C.), then allowed to cool to approx. 30° C. and 10%-strength sodium hydroxide solution is added to the brown solution until the reaction with phenolphthalein is alkaline. Then the solution is boiled (approx. 3-4 hours) until $NH_3$ gas can no longer be detected in the vapor phase ("boiling away of $NH_3$").

The greenish brown alkaline solution is cooled to 20°-25° C. and adjusted with approx. 1000 ml of 37%-strength hydrochloric acid until Congo-acid. As the temperature increases and a small amount of a finely dispersed precipitate separates, a vigorous development of $SO_2$ sets in which is continued to completion by heating the reaction mixture at boiling point for 2 hours ("boiling away of $SO_2$"). The 7-methoxy-1-naphthol-4-sulfonic acid formed after "boiling away $NH_3$ and $SO_2$" is not isolated as a substance. The replacement of an $NH_2$ group by an OH group in aromatic compounds, particularly those of the naphthalene series, via bisulfite addition compounds is known from the literature as the "Bucherer reaction".

Approx. 150 ml of a 40%-strength sodium nitrite solution are added dropwise to the yellowish brown solution of approx. 5.5 l containing hydrochloric acid obtained after the "boiling away of $SO_2$" until a positive nitrite reaction is obtained (potassium iodide starch paper test), in which process the internal temperature of the reaction solution should not exceed 10° C. Once approx. 10-15% of the amount of sodium nitrite solution necessary for the nitrosation reaction have been added, the nitroso compound starts to precipitate from the dark-red solution in microcrystalline form. Stirring is continued for a further 2-3 hours at 5°-10° C., then the solution is allowed to stand for a further 30-45 minutes without stirring and then the suspension is filtered off by suction using a sintered disk filter funnel. The red nitroso compound is pressed out well on the sintered disk filter funnel and then dried in air at 20°-25° C.

The 7-methoxy-2-nitroso-1-naphthol-4-sulfonic acid is produced as sodium sulfonate mixed with common salt in a purity of 92%.

Yield: 253 g (86% of theory), based on 7-methoxy-1-aminonaphthalene-4-sulfonic acid

7-Methoxy-2-amino-1-naphthol-4-sulfonic acid (5th. Reaction stage)

120 g of 7-methoxy-2-nitroso-1-naphthol-4-sulfonic acid and 18.5 g of sodium boron hydride are introduced consecutively while stirring into dilute sodium hydroxide solution prepared from 8500 ml of water and 28 g of sodium hydroxide. The deep red solution formed is cooled to 2°–3° C., the air space above the solution is replaced by nitrogen and 250 ml of 37%-strength hydrochloric acid is poured into the solution while stirring vigorously. The internal temperature of the solution rises to 10°–15° C. with the development of considerable foam. On undershooting the neutral point, a microcrystalline colorless precipitate precipitates, the color of the solution changing to bright yellow. The suspension formed is stirred for a further 15 minutes at 10°–15° C. and then filtered off by suction under nitrogen using a sintered disk filter funnel. The contents of the sintered disk filter funnel are washed with ice water, pressed out well and dried in a vacuum desiccator at 20°–25° C. over phosphorus pentoxide. The 7-methoxy-2-amino-1-naphthol-4-sulfonic acid prepared in this manner is virtually colorless and takes on a slight violet discoloration in air.

Yield: 83.5 g (78% of theory)

7-Methoxy-1,2-naphthoquinone-(2)-diazide-4-sulfonic acid (6th. Reaction stage)

39 g of pulverized 7-methoxy-2-amino-1-naphthol-4-sulfonic acid are suspended in 650 ml of water (pH: 2.5–2.6). A solution of 0.8 g of CuSO$_4$.5H$_2$O and 62.5 ml of 2N NaNO$_2$ solution (pH: 4.0) is poured rapidly into this suspension, during which process the internal temperature of the diazotization mixture rises to 25°–28° C. (pH: 5.0). The brown solution which contains a few dark constituents is stirred at this temperature for a further 2–3 hours and then adjusted to a pH of 2.6–2.8 with a few drops of 37%-strength hydrochloric acid, stirred for a further 15 minutes, treated with 15 g of activated carbon and filtered. The 7-methoxy-1,2-naphthoquinone-(2)-diazide-4-sulfonic acid is precipitated in the form of yellow needles from the clear, reddish brown filtrate with 420 ml of 37% strength hydrochloric acid. Stirring is carried out for a further 3 hours at 5°–10° C. and then the reaction mixture is filtered off by suction using a sintered disk filter funnel. The contents of the sintered disk filter funnel are washed with a little ice water and dried in a vacuum desiccator at 20°–25° C. over phosphorus pentoxide.

Yield: 24.8 g (61.3% of theory)

7-Methoxy-1,2-naphthoquinone-(2)-diazide-4-sulfonyl chloride (7th. Reaction stage)

7-Methoxy-1,2-naphthoquinone-(2)-diazide-4-sulfonic acid is reacted in accordance with known methods at elevated temperature with chlorosulfonic acid to form the corresponding sulfonyl chloride and then the excess chlorosulfonic acid is decomposed with ice water. The microcrystalline precipitation produced is filtered off by suction, washed with ice water until neutral and dried in air at 20°–25° C. with protection against light. An additional purification of the sulfonyl chloride obtained is not necessary for the further processing.

Yield: 11.4 g (75% of theory)

Decomposition point: 163°–165° C. (dark coloration—development of gas)

Condensation product of 7-methoxy-1,2-naphthoquinone-(2)-diazide-4-sulfonyl chloride and 2,3,4-trihydroxybenzophenone (8th. Reaction stage)

7-Methoxy-1,2-naphthoquinone-(2)-diazide-4-sulfonyl chloride is esterified in accordance with known processes in a water-miscible organic solvent, for example acetone, at 20°–25° C. with 2,3,4-trihydroxybenzophenone in the presence of an HCl acceptor, for example triethyleneamine, N-methylmorpholine or soda. The 2,3,4-trihydroxybenzophenone ester is isolated in a known manner by adding the esterification mixture dropwise to 3%-strength hydrochloric acid. The bright yellow amorphous precipitate is suctioned off by filter, out well and dried in air at 20°–25° C. with protection against light. The condensation product prepared in this manner contains 95% 2,3,4-trihydroxybenzophenone triester and 5% 2,3,4-trihydroxybenzophenone biester of the 7-methoxy-1,2-naphthoquinone-(2)-diazide-4-sulfonic acid.

Yield: 20.1 g (88% of theory)

SYNTHESIS EXAMPLE 2

Synthesis of the aryl ester of 2,3,4-trihydroxybenzophenone and 8-methoxy-1,2-naphthoquinone-(2)-diazide-4-sulfonic acid 1-Acetylamino-8-naphthol-4-sulfonic acid (1st. Reaction stage)

Commercially available 1-amino-8-naphthol-4-sulfonic acid (BAYER AG) is reacted with acetic anhydride at 50° C. in aqueous soda solution analogously to 1-amino-8-naphthol-3,6-disulfonic acid (H acid), in which process both the amino and the hydroxyl group are acetylated. Acetylation is complete if blue coloration ("self-coupling" of diazotized H acid) no longer occurs on adding a drop of NaNO$_2$ solution to a sample of the acetylation mixture acidified with hydrochloric acid and then made alkaline with soda solution, but only a yellow coloration can be observed. Once this point has been reached, the acetyl radical bound to oxygen is cleaved off by adding calcined soda and heating the acetylation mixture to 90°–95° C., whereas the acetylamino group is not attacked. The solid colorless 1-acetylamino-8-naphthol-4-sulfonic acid is precipitated from the soda-alkaline solution with 20% strength hydrochloric acid, filtered off by suction and dried in air at 20°–25° C.

Yield: 90–95% of theory

1-Acetylamino-8-methoxynaphthalene-4-sulfonic acid (Na salt)

(2nd. Reaction stage)

1-Acetylamino-8-naphthol-4-sulfonic acid is methylated at the phenolic oxygen by known methods in 15%-strength sodium hydroxide solution with dimethyl sulfate at 30°–40° C., in which process the pH of the reaction mixture should always be higher than 8. The end point of the methylation reaction: negative azo dyestuff coupling of the aqueous phase of the reaction mixture, for example with 4-N,N-diethylaminobenzenediazonium chloride (ZnCl$_2$ double salt). If methylation is incomplete, the azo dyestuff coupling is positive (blue coloration). During the methylation reaction, the 1-acetylamino-8-methoxynaphthalene-4-sulfonic acid precipitates as Na salt from the reaction mixture as almost colorless microcrystals.

Yield: 70-75% of theory

8-Methoxy-1-aminonaphthalene-4-sulfonic acid (3rd. Reaction stage)

8-Methoxy-1-acetylaminonaphthalene-4-sulfonic acid is suspended in 20%-strength hydrochloric acid and the suspension is heated under a reflux condenser while stirring at 90°-100° C. After approx 1-1½ hours, the deacetylation is complete. The mixture is allowed to cool to 20°-25° C., the slightly pink-colored crystals are filtered off by suction, they are washed on the sintered disk filter funnel with water and then dried in a vacuum drying oven at 50°-60° C.

Yield: 90-95% of theory

8-Methoxy-1-naphthol-4-sulfonic acid (4th. Reaction stage)

The replacement of the amino group by the phenolic hydroxyl group is achieved analogously to the Bucherer reaction known from the literature. 8-Methoxy-1-aminonaphthalene-4-sulfonic acid is heated in a commercially available 37%-strength aqueous $NaHSO_3$ solution at 100° C. for approx. 20-24 hours while stirring under a reflux condenser. The suspension formed is then rendered alkaline to phenolphthalein with 10%-strength sodium hydroxide solution and boiled while continuing to stir (approx. 3-4 hours) until $NH_3$ gas can no longer be detected in the vapor phase of the reaction vessel ("boiling away of $NH_3$"). The suspension is then cooled to 20°-25° C. and it is rendered Congo-acid with 37%-strength hydrochloric acid. As the temperature rises, a vigorous development of $SO_2$ sets in. After heating the reaction mixture at boiling point for 2 hours, the development of $SO_2$ is complete ("boiling away of $SO_2$"). The reaction mixture is cooled to 20°-25° C. and the suspension is filtered off by suction. The almost colorless crystals collected on the sintered disk filter funnel are washed with a little cold water and dried in a vacuum drying oven at 70°-75° C. Yield: 75-80% of theory

8-Methoxy-2-nitroso-1-naphthol-4-sulfonic acid (Na salt)

(5th. Reaction stage)

8-Methoxy-1-naphthol-4-sulfonic acid is suspended in 37%-strength hydrochloric acid/water (1:4) and nitrosated while stirring with a 2N $NaNO_2$ solution at 0°-5° C. until a positive nitrite reaction is obtained (potassium iodide starch paper test). After 2-2½ hours the nitrosation is complete. The yellow microcrystalline nitroso compound formed is filtered off by suction and the substance, still moist from the sintered disk filter funnel, is purified by dissolving in water and precipitating with common salt. The nitroso compound obtained in this way is dried in a vacuum drying oven at 30°-35° C.

Yield: 80-85% of theory

8-Methoxy-2-amino-1-naphthol-4-sulfonic acid (6th. Reaction stage)

8-Methoxy-2-nitroso-1-naphthol-4-sulfonic acid is suspended in 37%-strength aqueous $NaHSO_2$ solution and heated for approx. 1 hour at 80°-85° C. under a reflux condenser. The bright brown solution formed in this process is cooled to 20°-25° C. and rendered Congo-acid with 37%-strength hydrochloric acid/water (2:1). The development of $SO_2$ which sets in spontaneously is continued to completion by heating the reaction solution at 80°-85° C., in which process the 8-methoxy-2-amino-1-naphthol-4-sulfonic acid precipitates at the same time as a sparingly soluble inner salt (betaine). After cooling the reaction mixture to 20°-25° C., the slightly pink-colored precipitate is filtered off by suction, washed with water until neutral and dried in a vacuum drying oven at 40°-45° C.

Yield: 75-80% of theory

8-Methoxy-1,2-naphthoquinone-(2)-diazide-4-sulfonic acid (7th. Reaction stage)

8-Methoxy-2-amino-1-naphthol-4-sulfonic acid is suspended in water, the suspension is adjusted to a pH of 4.0-4.5 with 10% strength $NaHCO_3$ solution and an aqueous solution of $NaNO_2$ and $CuSO_4$ is then added rapidly dropwise to the suspension, in which process the temperature of the diazotization mixture is limited to 15°-20° C. The diazotization is complete as soon as a weak, persistant nitrite reaction (potassium iodide starch paper test) can be observed. The $CuSO_4.5H_2O$ required for the diazotization is used in an amount of 1.0-1.5%, based on the aminonaphthol-4-sulfonic acid used. The diazo solution is stirred for a further 30 minutes at 15°-20° C., the pH is adjusted to 5-6 and it is filtered using activated carbon. The yellow-colored crystalline 8-methoxy-1,2-naphthoquinone-(2)-diazide-4-sulfonic acid is precipitated as Na salt from the clear, yellowish brown filtrate by adding common salt. The mixture is allowed to stand for a further 30 minutes at 20°-25° C. without stirring and then the naphthoquinone diazide is filtered off by suction, the latter is washed on the sintered disk filter funnel with a little ice water and then the contents of the sintered disk filter funnel are dried in a vacuum drying oven at 30°-35° C.

Yield: 70-75% of theory

8-Methoxy-1,2-naphthoquinone-(2)-diazide-4-sulfonyl chloride (8th. Reaction stage)

8-methoxy-1,2-naphthoquinone-(2)-diazide-4-sulfonic acid (Na salt) is reacted with chlorosulfonic acid to form the corresponding sulfonyl chloride analogously to the chlorination method described in Synthesis Example 1, the chlorosulfonic acid used in excess is subsequently decomposed with ice/water and the yellow-colored microcrystalline precipitate produced is filtered off by suction. The latter is washed on the sintered disk filter funnel with ice water until neutral and then dried in a vacuum drying oven at 20°-25° C. Purification is not necessary for further processing of the sulfonyl chloride.

Yield 85-90% of theory

Decomposition point: 163°-165° C. (dark coloration, development of gas)

Condensation product of 8-methoxy-1,2-naphthoquinone-(2)-diazide-4-sulfonyl chloride and 2,3,4-trihydroxybenzophenone (9th. Reaction stage)

The condensation is carried out in acetone at 20°-25° C. in the presence of an HCl acceptor analogously to the method described in Synthesis Example 1. The isolation of the 2,3,4-trihydroxybenzophenone ester is achieved by adding the esterification mixture dropwise to 3%-strength hydrochloric acid. The bright yellow, amorphous precipitate is filtered off by suction, pressed out well, washed with water and dried in a vacuum drying oven at 20°-25° C.

Yield: 85-90% of theory (93% triester, 7% bisester)
Decomposition point: ~170° C. (dark coloration)

APPLICATION EXAMPLE 1

Silicon wafers are coated with a solution of
71.10 pbw of propylene glycol methyl ether acetate,
2.24 pbw of Compound No. 1 (Table 2),
1.24 pbw of 2,6-bishydroxymethyl-p-cresol and
24.41 pbw of cresol-formaldehyde novolak (melting range 122°-132° C. according to DIN 53 181) on a resist spinner at a rotary speed of 4000 rev/min and then dried on a hot plate at a temperature of 110° C. for 60 s. The coating thickness is approx. 1.5 μm. Exposure is carried out at a wavelength of 436 nm using a projection exposure unit of the type FPA 1550 made by Canon through a photomask which contains various line grids in the order of magnitude of 2.0 to 0.65 μm. The exposed wafers are developed for 60 s by an immersion method with a developer of the "AZ-developer 30" brand (manufactured by HOECHST AG), then rinsed with water and dried. A positive image of the photomask is obtained, lines and spaces having a width of 0.9 μm still being perfectly resolved at an exposure energy of 120 mJ/cm².

If 2,6-bishydroxymethyl-p-cresol is replaced in the above-mentioned formulation by equal amounts by weight of cresol-formaldehyde novolak, the lithographic result is only insignificantly affected.

APPLICATION EXAMPLE 2

Application Example 1 is repeated, the silicon wafers being baked after the exposure for 60 s at a temperature of 120° C. on a hot plate and then being subjected to an exposure over the entire surface at 200 mJ/cm² by means of a contact exposure unit of the type Sues MJB 3. This exposure energy is measured with an intensity measuring instrument made by OAI, model 206 for the wavelength range from 400 to 500 nm. After development, a negative image of the photomask is obtained, lines and spaces having a width of 0.6 μm still being perfectly resolved at an exposure energy of 120 mJ/cm².

APPLICATION EXAMPLE 3

Application Example 1 is repeated, the composition of the photoresist solution being changed as follows:
72.10 pbw of propylene glycol methyl ether acetate,
pbw 8.08 pbw of Compound No. 1,
1.24 pbw of 2,6-bishydroxymethyl-p-cresol and
23.58 pbw of cresol-formaldehyde novolak.

A positive image of the photomask is again obtained. With an exposure energy of 180 mJ/cm², lines and spaces having a size of 0.9 μm are clearly resolved.

APPLICATION EXAMPLE 4

Application Example 3 is repeated, a one-minute baking step at 120° C. on a hot plate again being carried out after the exposure through the photomask and an exposure over the entire surface being carried out at 200 mJ/cm² after cooling, analogously to Application Example 2. In the negative image of the photomask visible after the development, lines and spaces are resolved down to 0.65 μm if the energy is 180 mJ/cm² during the first exposure.

APPLICATION EXAMPLE 5

The Application Examples 1 to 4 are repeated, Compound No. 1 being replaced by an equal quantity of Compound 9. If the exposure time is adjusted to the specific properties of the individual solutions, comparably good results can be achieved both with positive and with negative processing. The same good results are also achieved if mixtures of the two Compounds No. 1 and No. 9 are used.

The addition of surface-active additives to these solutions to achieve a completely smooth surface after the coating does not affect the lithographic properties.

For comparison:

If unsubstituted 1,2-naphthoquinone-(2)-diazide-4-sulfonic acid ester (Compound No. 0) is used instead of Compounds No. 1 and No. 9, the required exposure energies are higher by a factor of to 14 if light of the wavelength 436 nm is used. The following Table 3 shows the necessary exposure energies both for positive and for negative processing:

TABLE 3

| Compound No. | Content in the solution (%) | Processing | Exposure energy (mJ/cm²) |
|---|---|---|---|
| 1 | 2.24 | pos. | 120 |
| 1 | 2.24 | neg. | 120 |
| 1 | 3.08 | pos. | 180 |
| 1 | 3.08 | neg. | 180 |
| 9 | 2.24 | pos. | 180 |
| 9 | 2.24 | neg. | 180 |
| 9 | 3.08 | pos. | 220 |
| 9 | 3.08 | neg. | 220 |
| 0 | 2.24 | pos. | 1600 |
| 0 | 2.24 | neg. | 1100 |
| 0 | 3.08 | pos. | 1700 |
| 0 | 3.08 | neg. | 1400 |

APPLICATION EXAMPLE 6

Silicon wafers are coated with a solution of
72.10 pbw of propylene glycol methyl ether acetate,
2.77 pbw of Compound No. 11,
1.10 pbw of 2,6-bishydroxymethyl-p-cresol and
24.00 pbw of cresol-formaldehyde novolak
as in Application Example 1, dried and then exposed. After development within one minute, a positive image of the photomask is produced, lines and spaces down to 0.8 μm being satisfactorily resolved. If a baking step of 60 s duration at a temperature of 125° C. on a hot plate and an exposure over the entire surface at 200 mJ/cm² are carried out after the exposure, a negative image of the mask can be seen in the subsequent development process after approx. 45 s. The resistance of this image to the attack of the developer is, however, only slight so that if the development time is prolonged, the coating is completely stripped from the silicon wafers. With modified exposure energies and development times, this behavior manifests itself even if Compound No. 11 is replaced by Compound No. 6 or No. 13.

APPLICATION EXAMPLE 7

Silicon wafers are coated with a solution of
72.10 pbw of propylene glycol methyl ether acetate,
3.62 pbw of Compound No. 3,
1.14 pbw of 2,6-bishydroxymethyl-p-cresol and 23.14 pbw of cresol-formaldehyde novolak
as in Application Example 1, dried and exposed. Following a temperature treatment of one minute duration at 120° C. on a hot plate and after cooling, they are subjected to exposure at 200 mJ/cm$^2$ over the entire surface. After development lasting 45 s, a negative image of the exposure master having a resolution better than 0.9 μm is produced if the energy of the exposure to an image is 400 mJ/cm$^2$. The same result is also achieved if the composition of the photoresist solution is altered as follows:

72.36 pbw of propylene glycol methyl ether acetate,
2.16 pbw of Compound No. 4,
1.08 pbw of 2,6-bishydroxymethyl-p-cresol and
24.40 pbw of cresol-formaldehyde novolak.

APPLICATION EXAMPLE 8

Silicon wafers are coated with a solution of
72.11 pbw of propylene glycol methyl ether acetate,
2.77 pbw of Compound No. 5,
1.27 pbw of 2,6-bishydroxymethyl-p-cresol and
23.85 pbw of cresol-formaldehyde novolak
as in Application Example 1, dried and exposed. A 4-minute development resolves lines and spaces down to 0.8 μm in the positive mask image if the exposure energy is 280 mJ/cm$^2$. If a temperature treatment of one minute at 120° C. on a hot plate is carried out before the development followed by an exposure at 200 mJ/cm$^2$ over the entire surface, a negative mask image is obtained after a one-minute development. The resolution is better than 0.7 μm if the exposure energy is 360 mJ/cm$^2$. The same behavior is also manifested if a solution of the following composition is used:

72.10 pbw of propylene glycol methyl ether acetate,
2.51 pbw of Compound No. 2,
1.10 pbw of 2,6-bishydroxymethyl-p-cresol and
24.29 pbw of cresol-formaldehyde novolak.

For negative processing, the required exposure energy is 200 mJ/cm$^2$.

APPLICATION EXAMPLE 9

Analogously to Application Example 1, silicon wafers are coated with a solution of
72.03 pbw of propylene glycol methyl ether acetate,
2.24 pbw of Compound No. 1,
1.24 pbw of 2,6-bishydroxymethyl-p-cresol,
24.39 pbw of cresol-formaldehyde novolak and
0.10 pbw of 4-(di-2-acetoxyethyl)amino-2-methyl-α-cyanocinnamonitrile,
dried and exposed. After a development time of one minute, structures down to 0.9 μm are resolved in the positive mask image formed.

If a temperature treatment of 60 s at 120° C. is carried out on a hot plate after exposure and an exposure is carried out over the entire surface at 200 mJ/cm$^2$, a negative image of the photomask is formed under the same conditions and this still manifests well-resolved 0.6 μm structures.

APPLICATION EXAMPLE 10

Silicon wafers are coated with the photoresist solution of the Application Example 1 and then dried for 1 minute at 80° C. on a hot plate, and exposed as described. A 0.27N aqueous solution of tetramethylammonium hydroxide is used for development. After a development time of 30 s, lines and spaces down to 0.9 μm are resolved in the positive image of the photomask. If a baking process of 60 s at 120° C. is carried out on a hot plate after the development and an exposure at 200 mJ/cm$^2$ is carried out over the entire surface, lines and spaces down to 0.75 μm are resolved after a development time of 45 s in the negative image formed of the mask.

APPLICATION EXAMPLE 11

Silicon wafers are coated with the photoresist solution of Application Example 1, dried for one minute at 100° C. and exposed as described. A one-minute temperature treatment at 125° C. is followed immediately, that is to say without post-exposure over the entire surface, by a development in 0.4N aqueous tetramethylammonium hydroxide solution. After a development time of 45 s, a negative image of the mask is produced, the resolution being better than 0.9 μm at an exposure energy of 120 mJ/cm$^2$.

APPLICATION EXAMPLE 12

The composition of the photoresist solution of Application Example 1 is modified by replacing the 2,6-bishydroxymethyl-p-cresol by an equal amount by weight of hexalkoxymethylmelamine (alkoxy-CH$_3$O—/C$_4$H$_9$O—1:1). Silicon wafers are coated with this solution as in Application Example 1, dried and exposed. After an exposure time of 2 minutes, a positive mask image is produced having a resolution of 0.9 μm if the exposure energy is 360 mJ/cm$^2$.

If a temperature treatment of 60 s duration at 120° C. and an exposure over the entire surface of 200 mJ/cm$^2$ are carried out after the exposure, a negative mask image is formed with a four-minute development. The resolution of 0.7 μm is achieved if exposure is carried out beforehand at 200 mJ/cm$^2$.

APPLICATION EXAMPLE 13

Silicon wafers are coated with a solution of
72.10 pbw of cyclohexanone,
2.51 pbw of Compound No. 16,
1.34 pbw of 2,6-bishydroxymethyl-p-cresol and
24.05 pbw of cresol-formaldehyde novolak
as in Application Example 1, dried and exposed. A development of one minute resolves lines and spaces down to 0.8 μm in the positive mask image if the exposure energy is 59 mJ/cm$^2$. If a temperature treatment of one minute at 120° C. is carried out on a hot plate followed by an exposure over the entire surface at 200 mJ/cm$^2$, a negative mask image is obtained after a development of one minute. The resolution is better than 0.7 μm if the exposure energy is 70 mJ/cm$^2$.

APPLICATION EXAMPLE 14

Silicon wafers are coated with a solution of
72.10 pbw of propylene glycol methyl ether acetate,
2.23 pbw of Compound No. 1,
2.79 pbw of 2,6-bishydroxymethyl-n-propylphenol and
22.88 pbw of cresol-formaldehyde novolak
as in Application Example 1, dried and exposed. After the exposure, a temperature treatment of 60 s duration is carried out at 120° C. followed by an exposure over the entire surface at 200 mJ/cm$^2$. After a development of one minute duration, a negative image of the mask is produced. The resolution is better than 0.65 μm if the structure exposure energy is 64 mJ/cm$^2$. The same result is achieved if the 2,6-bishydroxymethyl-n-propylphenol is replaced by an equal amount by weight of 2,6-bishydroxymethyl-4-(2-phenyl-2-propyl)phenol. The necessary exposure energy is then 300 mJ/cm².

If the 2,6-bishydroxymethyl-n-propylphenol is replaced by an amount of 4.19 pbw of 2,6-bishydroxymethyl-4-ethylphenol and the amount of the cresol-formaldehyde novolak is at the same time lowered from 22.88 pbw to 21.48 pbw, a resolution of 0.9 μm is produced under the same experimental conditions, the necessary exposure energy being only 48 mJ/cm².

APPLICATION EXAMPLE 15

A. Molar extinction coefficients ($\epsilon$) of some 1,2-naphthoquinone-(2)-diazide-4-sulfonic acid ester derivatives according to the invention:

TABLE 4

| | (Numbering in accordance with Table 2) | | |
|---|---|---|---|
| No. of the comp. | Molecular weight, MG | $[l \cdot cm^{-1\epsilon} \cdot mol^{-1}]$ ($\lambda$ = 436 nm) | $[l \cdot cm^{-1\epsilon} \cdot mol^{-1}]$ ($\lambda$ = Abs.$_{max}$) |
| 0 (Comparison) | 926 | 400 | 10700 (375 nm) |
| 1 | 1016 | 4700 | 16800 (395 nm) |
| 2 | 1016 | 2370 | 29250 (388 nm) |
| 3 | 1016 | 420 | 17500 (368 nm) |
| 4 | 968 | 700 | 16650 (375 nm) |
| 5 | 1010 | 900 | 20100 (383 nm) |
| 6 | 474 | 1200 | 6800 (392 nm) |
| 9 | 1038 | 4450 | 17400 (394 nm) |
| 11 | 882 | 2000 | 13000 (392 nm) |
| 13 | 836 | 3400 | 12300 (395 nm) |
| 16 | 1097 | 5880 | 17750 (396 nm) |
| 18 | 1100 | 1300 | 19030 (385 nm) |
| 14 (Comparison) | 1033 | 390 | 16900 (375 nm) |

B. "Standardized" molar extinction coefficients ($\epsilon'$) of the compounds listed in Table 4.

TABLE 5

| | (Numbering in accordance with Table 4) | | |
|---|---|---|---|
| No. of the comp. | Molecular weight, MG | $[l \cdot cm^{-1\epsilon'} \cdot mol^{-1}]$ ($\lambda$ = 436 nm) | $[l \cdot cm^{-1\epsilon'} \cdot mol^{-1}]$ ($\lambda$ = Abs.$_{max}$) |
| 0 (Comparison) | 233 | 101 | 2692 |
| 1 | 263 | 1217 | 4349 |
| 2 | 263 | 614 | 7572 |
| 3 | 263 | 109 | 4530 |
| 4 | 247 | 179 | 4249 |
| 5 | 261 | 233 | 5194 |
| 6 | 263 | 666 | 3773 |
| 9 | 263 | 1128 | 4409 |
| 11 | 263 | 596 | 3876 |
| 13 | 263 | 1070 | 3870 |
| 14 (Comparison) | 269 | 102 | 4401 |
| 16 | 290 | 1554 | 4692 |
| 19 | 291 | 344 | 5034 |

The "standardized" molar extinction $\epsilon'$ should be understood to mean the proportion of the molar extinction $\epsilon$ of the 1,2-naphthoquinone-(2)-diazide-4-sulfonic acid derivative $M_D$ which is accounted for by a 1,2-naphthoquinone-(2)-diazide-4-sulfonic acid radical D*,

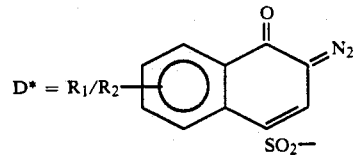

where $R_1$ and $R_2$ have the meanings specified above and it is assumed that the amount of the individual absorption of the ester radical or amide radical $M_{E/A}$ is negligible at the wavelength in question. The molecular weight $M_{D^*}$ of the 1,2-naphthoquinone-(2)-diazide -4-sulfonic acid radical D* is calculated from $$M_{D^*} = \frac{M_D - M_{E/A}}{n}$$

where $M_D$ = molecular weight of the 1,2-naphthoquinone-(2)-diazide-4-sulfonic acid derivative, $M_{E/A}$ = molecular weight of the ester radical or amide radical and n = the number of 1,2-naphthoquinone-(2)-diazide-4-sulfonic acid units.

The "standardized" extinction $\epsilon'$ is calculated from $$\epsilon' = \frac{M_{D^*}}{M_D} \cdot \epsilon$$

where $\epsilon$ = molar extinction of the 1,2-naphthoquinone-(2)-diazide-4-sulfonic acid derivative.

The values of the "standardized" molar extinction coefficients $\epsilon'$ listed in Table 5 exceed the molar extinction coefficients $\epsilon$ of the comparison compounds (No. 0 and No 14), in some cases appreciably, and consequently fulfil the condition, necessary for the occurrence of a photoreaction, of sufficiently high absorption to a greater degree than is the case for the comparison compounds. All the compounds in the context of the invention whose standardized molar extinction coefficients exceed the value of $\epsilon'$ = 120 are particularly preferred.

APPLICATION EXAMPLE 16

Silicon wafers are coated with a solution of
72.11 pbw of propylene glycol methyl ether acetate
7.81 pbw of Compound No. 1
20.09 pbw of cresol-formaldehyde novolak
as in Application Example 1 and dried for 45 s on a hot plate at a temperature of 90° C. Exposure is carried out at a wavelength of 365 nm using a projection exposure unit manufactured by ASM, having a numerical aperture of 0.42. After a second temperature treatment for 45 s on a hot plate at a temperature of 100° C., the wafers are developed for 30 s by an immersion method with a developer of the "AZ-developer 524 MIF" brand (manufactured by HOECHST AG), rinsed with water and dried. A positive image of the photomask is obtained, the smallest structures present on the mask, which have a width of 0.7 μm being perfectly resolved, at an exposure energy of 95 mJ/cm².

APPLICATION EXAMPLE 17

Silicon wafers are coated with a solution of
72.11 pbw of propylene glycol methyl ether acetate
2.79 pbw of Compound No. 1
1.67 pbw of 2,6-bis-hydroxymethyl-p-ethylphenol
23.44 pbw of cresol-formaldehyde novolak
as in Application Example 1 and dried. Exposure is carried out at a wavelength of 365 nm using a projection exposure unit manufactured by ASM, having a numerical aperture of 0.42. Exposure is followed by a temperture treatment for a duration of 60 s on a hot plate at 120° C. and, after cooling, an exposure over the entire surface is carried out at 200 mJ/cm². The wafers are developed for 80 s by an immersion method with a developer of the "AZ-developer 524 MIF" brand (manufactured by HOECHST AG). A negative image of the photomask is obtained, lines and spaces having a width of 0.5 μm being clearly resolved with steep edges, at an exposure energy of 350 mJ/cm².

What is claimed is:

1. A radiation-sensitive compound which is an ester or amide of a 1,2-naphthoquinone-(2)-diazide-4-sulfonic acid of the general formula:

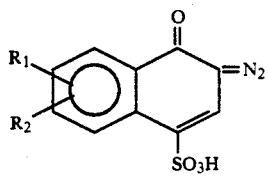
(I)

in which $R_1$ and $R_2$ are identical or different and denote hydrogen, an alkyl group containing 1 to 6 carbon atoms, an alkyl ether group or an alkyl thioether group whose carbon chains may be interrupted by ether oxygen atoms, containing a total of 1 to 6 carbon atoms, or an acylamino group containing 2 to 6 carbon atoms, $R_1$ and $R_2$ not being hydrogen at the same time.

2. A compound as claimed in claim 1, in which $R_1$ denotes hydrogen and $R_2$ denotes alkyl ether groups or alkyl thioether groups whose carbon chain may be interrupted by ether oxygen atoms, containing 1 to 6 carbon atoms.

3. A compound as claimed in claim 1, in which $R_1$ denotes hydrogen or methyl and $R_2$ denotes methyl or an alkyl ether group containing 1–4 carbon atoms.

4. A compound as claimed in claim 1, in which $R_1$ denotes, in position 6, hydrogen or methyl and $R_2$ denotes, in position 7, methyl or the methyl ether group.

5. A compound as claimed in claim 1, in which $R_1$ denotes, in position 6, hydrogen and $R_2$ denotes, in position 7, the methyl ether group.

6. A radiation-sensitive compound as claimed in claim 1, which is an ester and is formed from the 1,2-naphthoquinone-(2)-diazide-4-sulfonic acid of the formula I and a mono- or polyhydroxyaryl compound of the formula II:

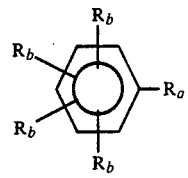
(II)

in which

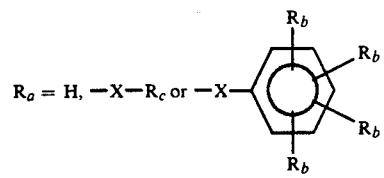

$R_b$ = H, an OH group, halogen or a lower alkyl group, at least one and not more than six $R_b$ groups being OH groups, X = a carbon bond, —O—, —S—, —SO₂—,

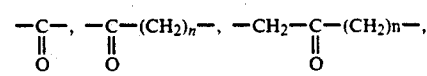

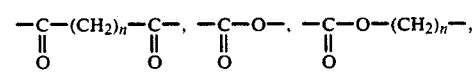

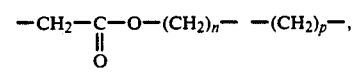

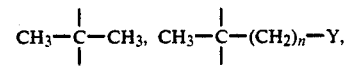

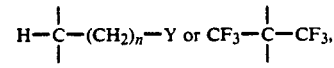

it being possible in each case for individual CH₂ groups to be replaced by ether functions or the hydrogen by substituents, n = 1 or 2, p = 1 to 3, Y = H or an optionally substituted alkoxy group, carboxy group, carboxyalkyl group, carboxyalkoxyalkyl group or aryl group, and $R_c$ = H or an optionally substituted alkyl group or aryl group, or of the formula III

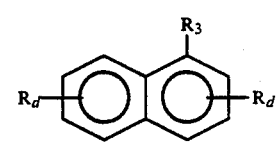
(III)

in which

R₃ = H or —CH₂— 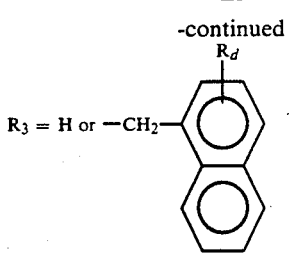

and

R_d=H or an OH group, at least one of the R_d groups being an OH group, or of the formula IV

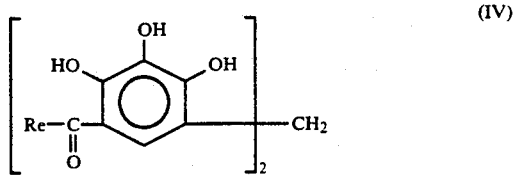 (IV)

in which

R_e=H or an optionally substituted alkyl group, alkoxy group or aryl group, or of the formula V R_f—OH (V)

in which

R_f=a straight-chain or branched alkyl group, cycloalkyl group or aralkyl group, optionally substituted by halogen or an acylamino radical and containing 1 to 14 carbon atoms, whose carbon chain may be interrupted by ether oxygen atoms, or of the group

—Z—OH in which

Z=an alkylene radical containing 2 to 12 carbon atoms or a cycloalkylene radical containing 8 to 18 carbon atoms, whose carbon chains may be interrupted by ether oxygen atoms, or an aralkylene radical containing 8 to 16 carbon atoms, it being possible for the cycloaliphatic and aromatic members to be joined by a single bond, by —O—, —S—, —SO₂—, —CO—,

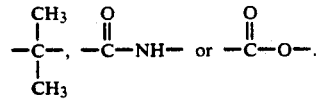

7. A radiation-sensitive compound as claimed in claim 1, which is an amide formed from the 1,2-naphthoquinone (2)-diazide-4-sulfonic acid of the formula I and a primary or secondary amine of the formula VI:

H—NR_gR_h (VI)

in which

R_g=hydrogen, an optionally substituted alkyl, cycloalkyl, aryl or aralkyl radical containing 1 to 14 carbon atoms, whose carbon chain may be interrupted by ether oxygen atoms, R_h=—E—NR_gH in which E=an alkylene radical containing 2 to 12 carbon atoms, whose carbon chain may be interrupted by ether oxygen atoms, a cycloalkylene, arylene or aralkylene radical containing 8 to 18 carbon atoms, it being possible, in the case of polynuclear compounds, for the cycloaliphatic and aromatic members to be joined by a single bond, by —O—, —S—, —SO₂—, —CO— or —R_g—.

8. A radiation-sensitive mixture which comprises in admixture:
   a) a water-insoluble resinous binder which is soluble or at least swellable in aqueous alkaline or organic solvents, and
   b) a radiation-sensitive compound or mixure of radiation-sensitive compounds,
   wherein at least one of said radiation-sensitive compounds is an ester as claimed in claim 6.

9. A mixture as claimed in claim 8, further comprising a crosslinking agent.

10. A mixture as claimed in claim 8, wherein said binder is a novolak, a polyvinylphenol or a polyvinylalkylphenol.

11. A mixture as claimed in claim 8, further comprising a solvent or a solvent mixture.

12. A mixture as claimed in claim 8, further comprising a dyestuff, a leveling agent, a plasticizer, an adhesion promoter, a development accelerator or a surfactant.

13. A mixture as claimed in claim 8, wherein said binder is present in a concentration of about 15 to 99 percent by weight, based on the solid constituents of the mixture.

14. A mixture as claimed in claim 8, wherein said radiation-sensitive compound is present in a concentration of about 1 to 85 percent by weight, based on the solid constituents of the mixture.

15. A radiation-sensitive mixture which comprises in admixture:
   a) a water-insoluble resinous binder which is soluble or at least swellable in aqueous alkaline or organic solvents, and
   b) a radiation-sensitive compound or mixure of radiation-sensitive compounds,
   wherein at least one of said radiation-sensitive compounds is an amide as claimed in claim 7.

16. A mixture as claimed in claim 15, further comprising a crosslinking agent.

17. A mixture as claimed in claim 15, wherein said binder is a novolak, a polyvinylphenol or a polyvinylalkylphenol.

18. A mixture as claimed in claim 15, further comprising a solvent or solvent mixture.

19. A mixture as claimed in claim 15, further comprising a dyestuff, a leveling agent, a plasticizer, an adhesion promoter, a development accelerator or a surfactant.

20. A mixture as claimed in claim 15, wherein said binder is present in a concentration of about 15 to 99 percent by weight, based on the solid constituents of the mixture.

21. A mixture as claimed in claim 15, wherein said radiation-sensitive compound is present in a concentration of about 1 to 85 percent by weight, based on the solid constituents of the mixture.

22. A radiation-sensitive copying material, which comprises a coating base and a radiation-sensitive coating, wherein said radiation-sensitive coating comprises a radiation-sensitive mixture as claimed in claim 8 essentially freed of solvent.

23. A copying material as claimed in claim 22, wherein said coating base is a silicon wafer or a gallium arsenide wafer on which at least one further coating is additionally deposited between the semiconducting material and the radiation-sensitive coating.

24. A radiation-sensitive copying material which comprises a coating base and a radiation-sensitive coating, wherein said radiation-sensitive coating comprises a radiation-sensitive mixture as claimed in claim 15 essentially freed of solvent.

25. A copying material as claimed in claim 24, wherein said coating base is a silicon wafer or a gallium arsenide wafer on which at least one further coating is additionally deposited between the semiconducting material and said radiation-sensitive coating.

* * * * *

UNITED STATES PATENT AND TRADEMARK OFFICE
CERTIFICATE OF CORRECTION

PATENT NO. : 5,114,816  Page 1 of 6
DATED     : May 19, 1992
INVENTOR(S) : Siegfried Scheler et al.

It is certified that error appears in the above-identified patent and that said Letters Patent is hereby corrected as shown below:

```
As an Appendix, insert Tables I and II attached.
Column 15, line 9, delete "staoe" and insert --stage--.
Column 21, line 13, delete "5 2.24 pbw" and insert
     --2.24 pbw--;
          line 55, delete "pbw 8.08 pbw" and insert
     --8.08 pbw--.
Column 25, line 19, Table 4, delete ε (both occurrences),
     and insert at line 18, ε (both occurrences);
          line 50, Table 5, delete ε' (both occurrences),
     and insert at line 49, ε' (both occurrences)
```

Signed and Sealed this

Fifth Day of April, 1994

*Attest:*

BRUCE LEHMAN

*Attesting Officer*    Commissioner of Patents and Trademarks

APPENDIX
1,2-Naphthoquinone-(2)-diazide-4-sulfonic acid I

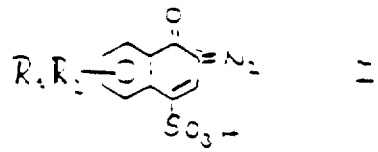

Table 1

| No. of comp. | $R_1$ | $R_2$ | N (%) cal. | N (%) found | S (%) cal. | S (%) found | Note |
|---|---|---|---|---|---|---|---|
| I/1 | 5-$OCH_3$ | H | 8.7 | 8.6 | 10.0 | 9.7 | Na Salt |
| I/2 | 6-$OCH_3$ | H | 14.1 | 14.0 | 10.8 | 10.9 | $NH_4$ Salt |
| I/3 | 7-$OCH_3$ | H | 8.9 | 8.7 | 10.1 | 10.4 | |
| I/4 | 8-$OCH_3$ | H | 8.7 | 8.5 | 9.9 | 9.9 | Na Salt |
| I/5 | 6-$CH_3$ | H | 15.0 | 14.7 | 11.4 | 11.2 | $NH_4$ Salt |
| I/6 | 6-$CH_3$ | 7-$CH_3$ | 14.2 | 14.1 | 10.9 | 10.8 | $NH_4$ Salt |
| I/7 | 7-$NHCOCH_3$ | H | 16.3 | 16.1 | 9.3 | 9.1 | $NH_4$ Salt + $H_2O$ |
| I/8 | 7-$SO_3H$ | H | 15.4 | 15.2 | 17.6 | 17.3 | $NH_4$ Salt |
| I/9 | 7-$SO_2N(CH_3)_2$ | H | 14.1 | 14.3 | 15.3 | 15.6 | $NH_4$ Salt + $H_2O$ |
| I/10 | 7-$SCH_3$ | H | 13.4 | 13.8 | 19.3 | 18.9 | $NH_4$ Salt + $H_2O$ |
| I/11 | 6-$COOCH_3$ | H | 12.2 | 12.2 | 9.3 | 9.9 | $NH_4$ Salt + $H_2O$ |
| I/12 | 6-Br | H | 11.5 | 11.3 | COMPARISON | | $NH_4$ Salt + $H_2O$ |

Derivatives of the 1,2-naphthoquinone-(2)-diazide-4-sulfonic acid I
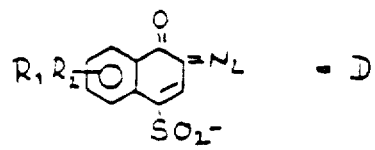
Table 2
| No. of comp. | $R_1$ | $R_2$ | Derivative of diazo acid | N (%) calc. | found | S (%) calc. | found |
|---|---|---|---|---|---|---|---|
| 0 | H | H | | COMPARISON | | | |
| 1 | 7-OCH$_3$ | H | ditto | 8.3 | 8.0 | 9.4 | 9.4 |
| 2 | 6-OCH$_3$ | H | ditto | 8.3 | 7.9 | 9.4 | 9.1 |
| 3 | 5-OCH$_3$ | H | ditto | 8.3 | 7.9 | 9.4 | 9.2 |
| 4 | 6-CH$_3$ | H | ditto | 8.7 | 8.2 | 9.9 | 9.3 |
| 5 | 6-CH$_3$ | 7-CH$_3$ | ditto | 8.3 | 8.0 | 9.5 | 9.1 |
| 6 | 7-OCH$_3$ | H | DO-⌬-C(CH$_3$)$_2$-⌬ | 5.9 | 6.1 | 6.7 | 6.3 |
| 7 | 7-OCH$_3$ | H | DO-⌬-C(CH$_3$)$_2$-⌬-OD | 7.5 | 7.3 | 8.5 | 8.3 |

| No. of comp. | R₁ | R₂ | Derivative of diazo acid | N (%) calc. | found | S (%) calc. | found |
|---|---|---|---|---|---|---|---|
| 8 | 7-OCH₃ | H | 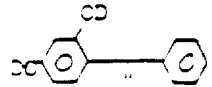 | 7.6 | 7.6 | 8.7 | 8.5 |
| 9 | 7-OCH₃ | H | 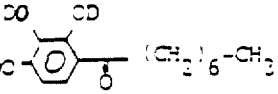 | 8.1 | 7.9 | 9.3 | 9.1 |
| 10 | 7-OCH₃ | H | 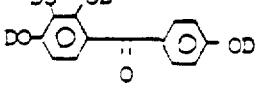 | 8.6 | 8.4 | 9.9 | 9.6 |
| 11 | 7-OCH₃ | H | 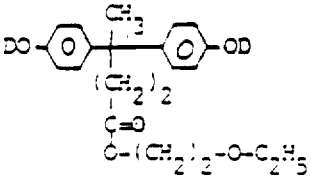 | 6.4 | 6.4 | 7.3 | 7.3 |
| 12 | 7-OCH₃ | H | 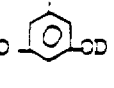 | 9.2 | 8.8 | 10.5 | 9.9 |
| 13 | 7-OCH₃ | H | 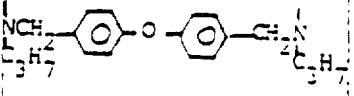 | 10.1 | 9.8 | 7.7 | 7.5 |
| 14 | 6-Br | H | 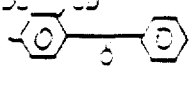 | COMPARISON | | | |
| 15 | 7-OSO₂-⌬-C(CH₃)₃ | H | 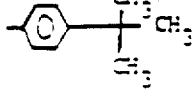 | 4.7 | 4.6 | 10.6 | 10.9 |
| 16 | 7-NHCOCH₃ | | 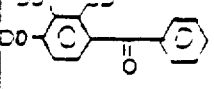 | 11.3 | 11.2 | 8.7 | 8.5 |

Table 4 (Numbering in accordance with Table 2)

| No. of the comp. | Molecular weight, MG | $\varepsilon$ [$l \cdot cm^{-1} \cdot mol^{-1}$] ($\lambda$= 436 nm) | $\varepsilon$ [$l \cdot cm^{-1} \cdot mol^{-1}$] ($\lambda$=Abs.max.) |
|---|---|---|---|
| 0 (Comparison) | 926 | 400 | 10 700 (375 nm) |
| 1 | 1016 | 4 700 | 16 800 (395 nm) |
| 2 | 1016 | 2 370 | 29 250 (388 nm) |
| 3 | 1016 | 420 | 17 500 (368 nm) |
| 4 | 968 | 700 | 16 650 (375 nm) |
| 5 | 1010 | 900 | 20 100 (383 nm) |
| 6 | 474 | 1 200 | 6 800 (392 nm) |
| 9 | 1038 | 4 450 | 17 400 (394 nm) |
| 11 | 882 | 2 000 | 13 000 (392 nm) |
| 13 | 836 | 3 400 | 12 300 (395 nm) |
| 16 | 1097 | 5 880 | 17 750 (396 nm) |
| 18 | 1100 | 1 300 | 19 030 (385 nm) |
| 14 (Comparison) | 1033 | 390 | 16 900 (375 nm) |

B. "Standardized" molar extinction coefficients ($\epsilon'$) of the compounds listed in Table 4.

Table 5 (Numbering in accordance with Table 4)

| No. of the comp. | Molecular weight, MG | $\epsilon'$ [$l \cdot cm^{-1} \cdot mol^{-1}$] ($\lambda$ = 436 nm) | $\epsilon'$ [$l \cdot cm^{-1} \cdot mol^{-1}$] ($\lambda$ = Abs.max.) |
|---|---|---|---|
| 0 (Comparison) | 233 | 101 | 2692 |
| 1 | 263 | 1217 | 4349 |
| 2 | 263 | 614 | 7572 |
| 3 | 263 | 109 | 4530 |
| 4 | 247 | 179 | 4249 |
| 5 | 261 | 233 | 5194 |
| 6 | 263 | 666 | 3773 |
| 9 | 263 | 1128 | 4409 |
| 11 | 263 | 596 | 3876 |
| 13 | 263 | 1070 | 3870 |
| 14 (Comparison) | 269 | 102 | 4401 |
| 16 | 290 | 1554 | 4692 |
| 19 | 291 | 344 | 5034 |